(12) United States Patent
Mosack

(10) Patent No.: US 7,037,521 B2
(45) Date of Patent: May 2, 2006

(54) USING A LASER FOR CUTTING A HOLE IN A CAPSULE FOR CONTROLLED DRUG DELIVERY

(75) Inventor: Linda Mosack, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 591 days.

(21) Appl. No.: 10/402,355

(22) Filed: Mar. 28, 2003

(65) Prior Publication Data

US 2004/0191308 A1   Sep. 30, 2004

(51) Int. Cl.
*A61K 9/48* (2006.01)
(52) U.S. Cl. ........................ 424/451; 424/451
(58) Field of Classification Search ................ 424/451
See application file for complete search history.

(56) References Cited

U.S. PATENT DOCUMENTS

| | | | |
|---|---|---|---|
| 5,004,614 A | 4/1991 | Staniworth | |
| 5,378,475 A | 1/1995 | Smith et al. | |
| 5,773,019 A | 6/1998 | Ashton et al. | |
| 5,795,591 A | 8/1998 | Lee et al. | |
| 5,902,598 A | 5/1999 | Chen et al. | |
| 6,001,386 A | 12/1999 | Ashton et al. | |
| 6,217,895 B1 | 4/2001 | Guo et al. | |
| 6,331,313 B1 | 12/2001 | Wong et al. | |
| 6,375,972 B1 | 4/2002 | Guo et al. | |
| 6,419,952 B1 * | 7/2002 | Wong et al. ............... | 424/463 |
| 2002/0086051 A1 | 7/2002 | Viscasillas | |
| 2002/0106395 A1 | 8/2002 | Brubaker | |
| 2002/0110591 A1 | 8/2002 | Brubaker et al. | |
| 2002/0110592 A1 | 8/2002 | Brubaker et al. | |
| 2002/0110635 A1 | 8/2002 | Brubaker et al. | |

FOREIGN PATENT DOCUMENTS

EP   0 425 298 A2 *   2/1991

* cited by examiner

*Primary Examiner*—Susan Tran
(74) *Attorney, Agent, or Firm*—John E. Thomas

(57) ABSTRACT

A method of fabricating capsules for sustained and controlled drug delivery. An array of capsules of a hydrophobic polymer is subjected to an extraction process to remove low-molecular-weight monomers, oligomers and polymers, and a laser is used to open accurately sized, spaced, and shaped holes in the capsules. In the process, the laser cutting oxidizes the hydrophobic polymer, making it sufficiently hydrophilic to allow wetting by the contents of the capsules. The capsules are then filled with a hydrophilic polymer covering the laser-cut opening and with one or more drugs for delivery, sealed, and removed from the array for mounting on suture tabs or other mounts. The use of the laser helps insure accurate and reliable delivery of drugs from the capsule.

17 Claims, 3 Drawing Sheets

USING A LASER FOR CUTTING A HOLE IN A CAPSULE FOR CONTROLLED DRUG DELIVERY

FIELD OF THE INVENTION

This invention relates to methods of fabricating a device for controlled drug delivery, and more specifically to methods of fabricating an intraocular device for sustained intraocular delivery of drugs.

BACKGROUND OF THE INVENTION

Devices and methods for sustained intraocular delivery of drugs are described in numerous U.S. patents. U.S. Pat. No. 6,331,313 (Wong et al.), discloses an orificed impermeable outer layer surrounding a core of drug for intraocular delivery and references additional patents on the art. U.S. Pat. No. 5,902,598 (Chen et al.) discloses multiple coating layers surounding an inner drug core or reservoir and providing permeability and openings for intraocular drug delivery, and references additional patents on the art. U.S. Pat. No. 5,378,475 (Smith et al.) discloses a suture tab attached to coating layers surounding one or more drugs core or reservoir and providing permeability and openings for intraocular drug delivery, and references additional patents on the art.

In non-intraocular sustained delivery systems for drugs, U.S. Pat. No. 5,795,591 (Lee et al.), among other patents, discloses the use of laser drilling to produce orifices through which the drugs may be delivered.

One method of delivering drugs in an intraocular site uses a suture tab attached to a capsule or cup containing the drug. The suture tab is typically made of polyvinyl alcohol (PVA), which is hydrophilic. The suture tab is inserted in the vitreous region of the eyeball and attached to the inner surface at a location appropriate for delivery of drug to a desired target area, such as the retina. The cup containing the drug is typically made of polydimethyl siloxane (PDMS), which is hydrophobic, making it impermeable to the drugs to be delivered. The controlled delivery of the drug from the cup requires one or more apertures in the PDMS through which the drug passes out of the cup, and requires some means of restricting drug flow through the aperture or apertures. In addition, drug delivery must be consistent among different capsules, and must be consistent for any individual capsule throughout the period of delivery.

To address these requirements, each cup is fabricated with a hole in the PDMS through which the drug is delivered, and a layer of PVA is placed between the drug and the hole. The PVA, being hydrophilic, is permeable to the drug. The drug diffuses through the PVA and passes through the hole into the vitreous region of the eye. Clearly the hole size and shape must be consistent, and the pathway through the hole must be unobstructed, for appropriate rates of drug delivery to be achieved and sustained. In addition, the proximity of hydrophilic PVA to hydrophobic PDMS cannot be allowed to introduce obstacles to drug delivery due to surface tension and consequent meniscus between them.

The conventional process used to cut the hole is a manual process using tools. This process leads to variations in size and position (centering on the cup top), and results in excess material around the cut either from flash or the material from the hole not being fully removed. These variations could potentially cause significant variations in the drug dosage received by the patient. Cutting the hole post extraction is preferable, however, cutting with a tool would lead to possible contamination in a process where less handling would be preferred from a microbiological viewpoint. The primary problem that must be solved is the formation of the hole in the PDMS cups with precise dimensions, clean cuts, reproducibly and with a process that is capable of being automated.

SUMMARY OF THE INVENTION

The invention is a method of fabricating capsules for sustained and controlled drug delivery. An array of capsules of a hydrophobic polymer is subjected to an extraction process to remove light-molecular-weight polymers, and a laser is used to open accurately sized, spaced, and shaped holes in the capsules. In the process, the laser cutting oxidizes the hydrophobic polymer, making it sufficiently hydrophilic to allow wetting by the contents of the capsules. The capsules are then filled with a hydrophilic polymer covering the laser-cut opening and with one or more drugs for delivery, sealed, and removed from the array for mounting on suture tabs or other mounts. The invention's use of the laser helps insure accurate and reliable delivery of drugs from the capsule.

DETAILED DESCRIPTION OF THE INVENTION

The invention produces a uniformly-sized, accurately spaced, and clean hole in a capsule used for intraocular drug delivery, utilizing a laser to make the hole. Lasers are capable of cutting precision holes of different sizes through polymeric materials accurately and reproducibly, and are capable of being automated. The laser wavelength and frequency may be selected to produce the appropriate dimension of hole. Depending on the choice of laser, power, and conditions of the material, the cutting process is either a thermal event, whereby the material is melted away, or a nonthermal event, whereby the material is ablated away by breaking the chemical bonds in the material.

Figure 1:
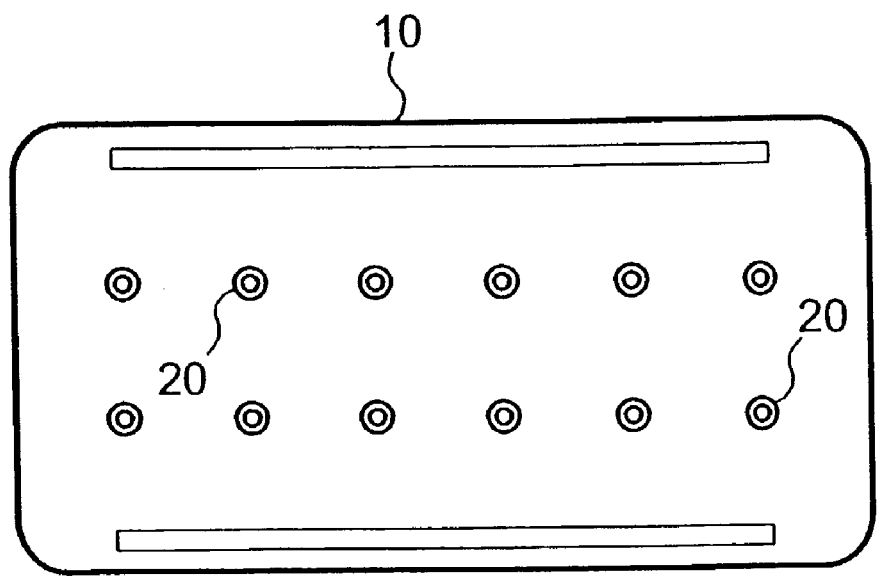
FIG. 1 shows a plan view of an array of capsules being fabricated for controlled drug delivery.
Figure 2A:
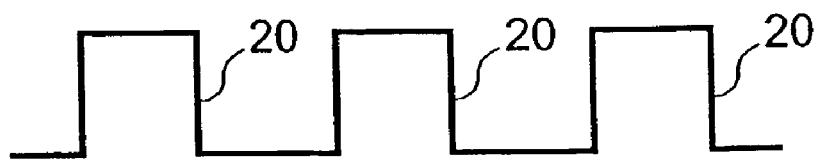
FIG. 2a shows a cross section of capsules in an array before holes are cut.
Figure 2B:
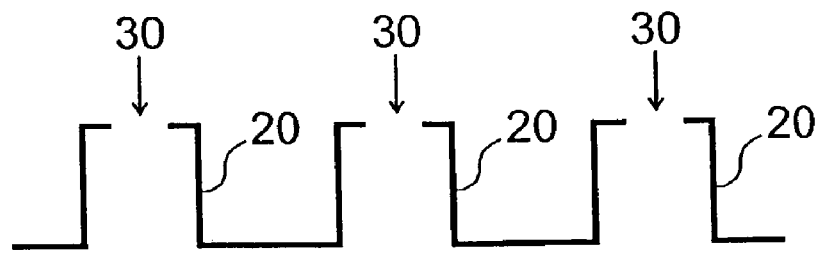
FIG. 2b shows a cross section of capsules in an array after holes are cut.

The capsules are made of a hydrophobic polymer, for example, polydimethyl siloxane (PDMS). See FIG. 1. For more economical fabrication and easier handling during fabrication in the invention's process, the capsules 20 are initially formed in an array 10, shown in plan view. FIG. 2a shows a schematic cross section of several capsules 20 as initially formed. The process then uses a laser to open a hole 30 in each capsule, resulting in the schematic cross section of several capsules 20 as shown in FIG. 2b. In subsequent steps the capsules are cut apart and attached to suture tabs, the drug core is inserted in each capsule, and a permeable hydrophilic polymer such as polyvinyl alcohol (PVA) is layered between the core and the hole in order to moderate or restrict the release rate of the drug.

Two problems arise in the fabrication of capsules. First, PDMS contains low-molecular-weight components which limit the ability to adhere PDMS surfaces to other surfaces. These components must be removed from the PDMS by an extraction process which causes a predictable degree of shrinkage in the capsule. If holes are made in a PDMS capsule before the extraction process is performed, the shrinkage of the capsule due to extraction changes the size of the holes, and thus changes the rate of drug delivery to be expected. Also, the use of a laser on PDMS before extraction has shown a high rate of imperfections in the holes produced.

Figure 3A:
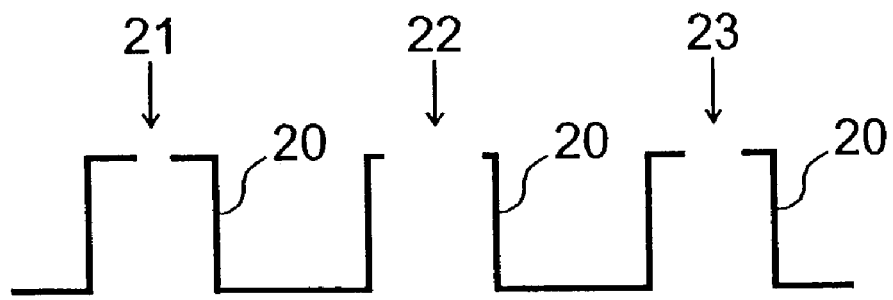
FIGS. 3a, 3b, and 3c show various cross sections of capsules with imperfections in fabricated holes.
Figure 3B:
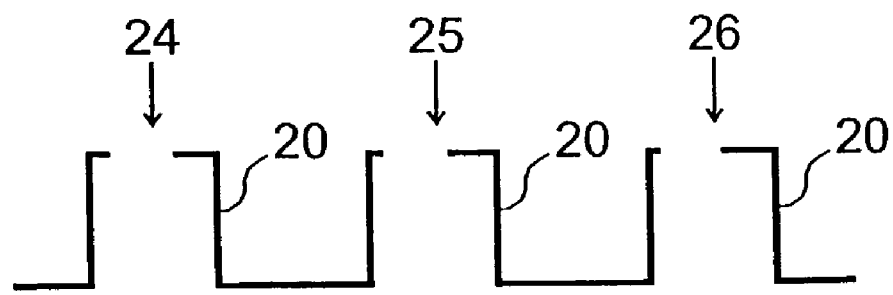
Figure 3C:
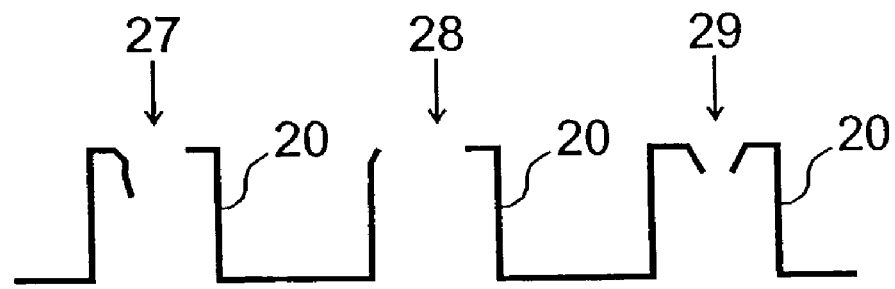

FIGS. 3a through 3c show different types of imperfections in the fabrication of holes in the capsules 20. In FIG. 3a, the sizes of holes 21, 22, 23 are different. Such a condition can arise from the use of a less-consistent method of creating the holes, such as drilling or punching. The condition can also arise from irregularities in laser power applied, from varying resistance to penetration caused by irregularities in the PDMS surface or volume, or from nonuniform shrinkage of the array when extraction is performed after hole fabrication. This result has been noted in tests of laser cutting where the hole cutting was performed before the extraction process. In any of these cases, the differences in hole size result in differing rates of drug delivery from individual capsules, an unacceptable outcome of fabrication.

In FIG. 3b, the hole positions 24, 25, 26 at the top of the capsules 20 are improperly spaced, the result of improper alignment of the array containing the capsules with the mechanism fabricating the holes. Such a condition can arise most commonly when the hole fabrication requires physical contact between the array and the hole fabrication mechanism, which does not occur when laser cutting is used. Again, in this case, differences in hole placement can result in differing rates of drug delivery, an unacceptable outcome of fabrication.

In FIG. 3c, a mechanical means of hole fabrication has been used, and hole positions 27, 28, 29 in capsules 20 show different potential imperfections arising from the use of such means. These results do not occur with the use of the laser to cut the holes.

To avoid these problems, the extraction process must be performed first, and a laser must then be used to make the holes.

The extraction followed by the use of the laser solves a second problem: the natural meniscus or wettability of the inserted PVA produced at the interface between the hydrophilic PVA and the hydrophobic PDMS. The meniscus can change the surface area of drug to be presented for conduit to the exterior of the capsule, or can even allow the drug in a purer form to reach the exterior of the capsule. Consequently, the meniscus is unacceptable. The laser cutting post extraction produces a more stable and oxidized surface of the PDMS, causing the PDMS surface to become hydrophilic, thereby eliminating the meniscus between the PDMS and the PVA.

The process produces holes on the order of 1–10 microns. Larger holes on the order of millimeters are produced by programming the laser to sweep across the given dimensions. Lasers such as $CO_2$ or Nd:YAG are used. Processes such as frequency doubling or tripling YAG lasers are used to produce smaller-dimension holes. The proposed process is automated by placing the arrays on a stage and either fixing the position of the capsules and sweeping the laser over the capsules or fixing the laser position and sweeping the capsules under the laser to the given coordinates for the holes.

Figure 4A:
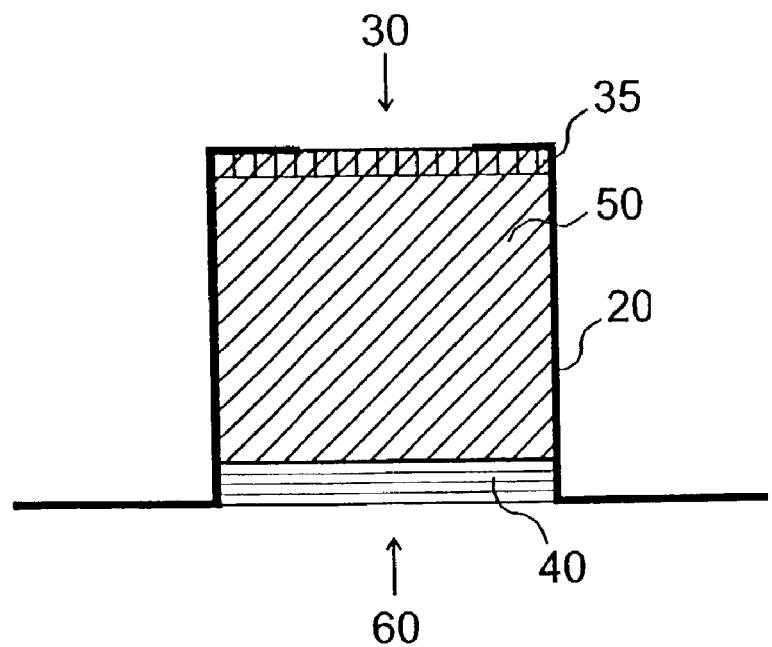
FIGS. 4a and 4b show cross sections of capsules after filling with drugs and sealing.
Figure 4B:
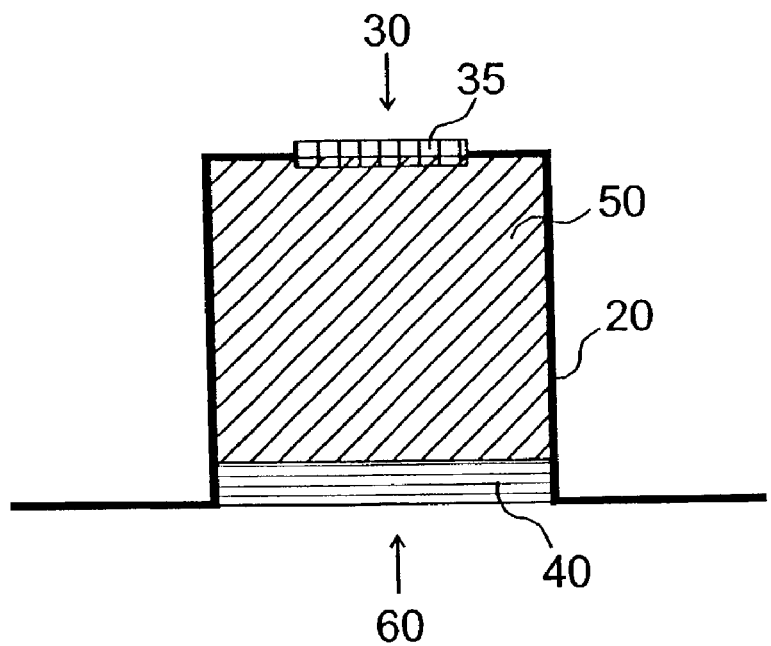

To avoid thermal or chemical damage to the drug, the drug and PVA are not inserted in the capsule until after the laser cutting process. Once the hole is cut in a capsule, the capsule is filled with the desired drug, and PVA is placed between the drug and the hole to moderate the rate of delivery of the drug through the hole. Each resulting capsule 20 resembles a 'top hat' as shown in FIGS. 4a and 4b. In FIG. 4a, PVA 35 is placed in capsule 20 via opening 60 at its base, drug 50 is placed in capsule 20 via opening 60, and PDMS 40 is placed over drug 50 at opening 60 and bonded to capsule 20, closing off opening 60. In FIG. 4b, PVA 35 is placed in capsule 20 via opening 30, drug 50 is placed in capsule 20 via opening 60, and PDMS 40 is placed over drug 50 at opening 60 and bonded to capsule 20, closing off opening 60.

In another embodiment, PVA 35 and drug 50 are mixed in suspension, so that both are placed in capsule 20 in mixture. In this second embodiment, drug 50 permeates PVA 35 from the outset.

Once the contents of all capsules in an array are in place, the capsules are cut from the array and attached to suture tabs for intraocular placement. In a further embodiment, the step of placing PDMS 40 over drug 50 at opening 60 may be deferred until the capsule is removed from the array, allowing the use of an impermeable portion of the suture tab as the means of closing off opening 60. In still another embodiment, the steps of placing drug 50 and PVA 35 in capsule 20 are deferred until the capsule is removed from the array.

The result of the invention's fabrication process is an intraocular suture tab with a highly uniform, highly accurate, economically-fabricated drug delivery mechanism.

What is claimed is:

1. A method of cutting a hole in a capsule for controlled drug delivery, comprising the steps of:
    fabricating an array of capsules made of a first hydrophobic polymer and having a large first opening;
    extracting low-molecular-weight components from the first hydrophobic polymer;
    using a laser to cut one or more second openings of uniform size, shape, and position in each capsule, and to oxidize the first hydrophobic polymer;
    fabricating individual drug-filled capsules from the array of capsules having laser-cut second openings wherein the first hydrophibic polymer is polydimethyl siloxane (PDMS).

2. The method of claim 1, wherein the step of fabricating individual drug-filled capsules from the array of capsules having laser-cut holes further comprises the steps of:
    placing a hydrophilic polymer to cover the one or more second openings in each capsule via the large first opening;
    placing one or more drugs in each capsule to cover the hydrophilic polymer via the large first opening;
    placing a second hydrophobic polymer to cover the drug via the large first opening, thereby closing off the large first opening;
    bonding the second hydrophobic polymer to the first hydrophobic polymer;
    cutting the array of capsules apart to produce individual drug-filled capsules.

3. The method of claim 2, wherein the step of placing a hydrophilic polymer to cover the one or more second openings in each capsule via the large first opening comprises the step of placing polyvinyl alcohol (PVA) to cover the one or more second openings in each capsule via the large first opening.

4. The method of claim 2, wherein the second hydrophobic polymer is polydimethyl siloxane.

5. The method of claim 1, wherein the step of fabricating individual drug-filled capsules from the array of capsules having laser-cut holes further comprises the steps of:
placing one or more drugs in each capsule to cover the one or more second openings via the large first opening;
placing a hydrophilic polymer to cover the drug in each capsule via each of the one or more second openings;
placing a second hydrophobic polymer to cover the drug via the large first opening, thereby closing off the large first opening;
bonding the second hydrophobic polymer to the first hydrophobic polymer;
cutting the array of capsules apart to produce individual drug-filled capsules.

6. The method of claim 5, wherein the step of placing a hydrophilic polymer to cover the one or more second openings in each capsule via the large first opening comprises the step of placing polyvinyl alcohol (PVA) to cover the one or more second openings in each capsule via the large first opening.

7. The method of claim 5, wherein the second hydrophobic polymer is polydimethyl siloxane.

8. The method of claim 1, wherein the step of fabricating individual drug-filled capsules from the array of capsules having laser-cut holes further comprises the steps of:
placing a hydrophilic polymer combined with one or more drugs to cover the one or more second openings in each capsule via the large first opening;
placing a second hydrophobic polymer to cover the hydrophilic polymer and drug via the large first opening, thereby closing off the large first opening;
bonding the second hydrophobic polymer to the first hydrophobic polymer;
cutting the array of capsules apart to produce individual drug-filled capsules.

9. The method of claim 8, wherein the step of placing a hydrophilic polymer combined with one or more drugs to cover the one or more second openings in each capsule via the large first opening comprises the step of placing polyvinyl alcohol (PVA) combined with one or more drugs to cover the one or more second openings in each capsule via the large first opening.

10. The method of claim 8, wherein the second hydrophobic polymer is polydimethyl siloxane.

11. A method of fabricating a drug-delivery capsule for controlled delivery of one or more drugs, comprising the steps of:
fabricating an array of capsules made of a first hydrophobic polymer and having a large first opening;
extracting low-molecular-weight components from the first hydrophobic polymer;
using a laser to cut one or more second openings of uniform size, shape, and position in each capsule, and to oxidize the first hydrophobic polymer;
fabricating individual drug-filled capsules from the array of capsules having laser-cut second openings;
attaching a suture tab to each individual drug-filled capsule wherein the first hydrophobic polymer is polydimethyl siloxane (PDMS).

12. The method of claim 11, wherein the step of fabricating individual drug-filled capsules from the array of capsules having laser-cut holes further comprises the steps of:
placing a hydrophilic polymer to cover the one or more second openings in each capsule via the large first opening;
placing one or more drugs in each capsule to cover the hydrophilic polymer via the large first opening;
placing a second hydrophobic polymer to cover the drug via the large first opening, thereby closing off the large first opening;
bonding the second hydrophobic polymer to the first hydrophobic polymer;
cutting the array of capsules apart to produce individual drug-filled capsules.

13. The method of claim 12, wherein the step of placing a hydrophilic polymer to cover the one or more second openings in each capsule via the large first opening comprises the step of placing polyvinyl alcohol (PVA) to cover the one or more second openings in each capsule via the large first opening.

14. The method of claim 12, wherein the second hydrophobic polymer is polydimethyl siloxane.

15. The method of claim 11, wherein the step of fabricating individual drug-filled capsules from the array of capsules having laser-cut holes further comprises the steps of:
placing one or more drugs in each capsule to cover the one or more second openings via the large first opening;
placing a hydrophilic polymer to cover the drug in each capsule via each of the one or more second openings;
placing a second hydrophobic polymer to cover the drug via the large first opening, thereby closing off the large first opening;
bonding the second hydrophobic polymer to the first hydrophobic polymer;
cutting the array of capsules apart to produce individual drug-filled capsules.

16. The method of claim 15, wherein the step of placing a hydrophilic polymer to cover the one or more second openings in each capsule via the large first opening comprises the step of placing polyvinyl alcohol (PVA) to cover the one or more second openings in each capsule via the large first opening.

17. The method of claim 15, wherein the second hydrophobic polymer is polydimethyl siloxane.

* * * * *

UNITED STATES PATENT AND TRADEMARK OFFICE
CERTIFICATE OF CORRECTION

PATENT NO.      : 7,037,521 B2                                    Page 1 of 1
APPLICATION NO. : 10/402355
DATED           : May 2, 2006
INVENTOR(S)     : Linda Mosack It is certified that error appears in the above-identified patent and that said Letters Patent is hereby corrected as shown below:

Col. 4, line 45
  replace "hydrophibic"
  with --hydrophobic--.

Signed and Sealed this

Eighth Day of May, 2007

JON W. DUDAS
*Director of the United States Patent and Trademark Office*